(12) United States Patent
Takahashi (10) Patent No.: US 8,391,577 B2
(45) Date of Patent: Mar. 5, 2013

(54) RADIATION IMAGE PROCESSING APPARATUS, IMAGE PROCESSING METHOD, X-RAY RADIOSCOPY APPARATUS AND CONTROL METHOD THEREOF

(75) Inventor: Kazuhiko Takahashi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 713 days.

(21) Appl. No.: 12/580,439

(22) Filed: Oct. 16, 2009

(65) Prior Publication Data

US 2010/0104165 A1     Apr. 29, 2010

(30) Foreign Application Priority Data

Oct. 29, 2008 (JP) ................................ 2008-278610

(51) Int. Cl.
*G06K 9/00* (2006.01)
*A61B 6/00* (2006.01)
*G21K 1/00* (2006.01)
(52) U.S. Cl. ................ 382/131; 382/132; 378/6; 378/7; 378/154
(58) Field of Classification Search .................. 382/131, 382/132; 378/6, 7, 154
See application file for complete search history.

(56) References Cited

U.S. PATENT DOCUMENTS

| | | | | |
|---|---|---|---|---|
| 4,823,370 A | * | 4/1989 | Kikuchi .................. | 378/98.4 |
| 5,513,239 A | | 4/1996 | Mulder .................. | 378/98.7 |
| 2003/0091243 A1 | | 5/2003 | Sasada .................. | 382/260 |
| 2007/0189440 A1 | * | 8/2007 | Rinkel et al. .................. | 378/4 |
| 2010/0111256 A1 | * | 5/2010 | Hayashida .................. | 378/87 |
| 2010/0140485 A1 | * | 6/2010 | Mishra et al. .................. | 250/363.1 |
| 2010/0316183 A1 | * | 12/2010 | Fuchs et al. .................. | 378/6 |

FOREIGN PATENT DOCUMENTS

| | | |
|---|---|---|
| JP | 62-092662 | 4/1987 |
| JP | 7-183094 | 7/1995 |
| JP | 2003-150954 | 5/2003 |
| JP | 2006-272013 | 10/2006 |

* cited by examiner

*Primary Examiner* — Alexander H Taningco
(74) *Attorney, Agent, or Firm* — Fitzpatrick, Cella, Harper & Scinto (57) ABSTRACT

A radiation image processing apparatus which improves contrast and sharpness of radiation images is provided. According to this radiation image processing apparatus, comparison is made between a first image data obtained by radiation imaging without going through the subject but through a grid for removing scattered radiation from a subject, and a second image data which is obtained by radiation imaging through the subject and the grid, and a two-dimensional distribution of abundance of scattered component is calculated. Using this two-dimensional distribution of scattered component, abundance of scattered radiation is locally determined at each position, and a sharpening process is performed with sharpening intensities that are increased in response to abundance of scattered radiation.

4 Claims, 12 Drawing Sheets

IRRADIATED X-RAY IS MEASURED
AT EACH CROSSING POINT

IRRADIATED X-RAY AMOUNT MAP

FIG. 8B

IRRADIATED X-RAY
AMOUNT EQUIVALENCE CURVES

EQUIVALENCE CURVE DATA TABLE
OF IRRADIATED X-RAY AMOUNT

| a1 | a4 | a7 |
|----|----|----|
| a2 | a5 | a8 |
| a3 | a6 | a9 |

RADIATION IMAGE PROCESSING APPARATUS, IMAGE PROCESSING METHOD, X-RAY RADIOSCOPY APPARATUS AND CONTROL METHOD THEREOF

BACKGROUND OF THE INVENTION

1. Field of the Invention

The present invention relates to a radiation image processing technique.

2. Description of the Related Art

When making observations of a subject (human body in particular) by detecting distribution of transmitted radiation such as X-rays that are transmitted through the subject, radiation imaging systems utilizing X-ray TV systems and accumulative fluorescent body (photostimulable phosphor) are used. In recent years, capturing of radiation images of a subject by directly receiving radiation that has been transmitted through a subject with a flat panel X-ray sensor, a large-scale image sensor (solid-state image sensor) that utilizes semiconductors, has become widespread.

When radiation passes through a subject, a portion of the radiation is scattered, and the contrast of the obtained image drops due to this scattering. In order to eliminate this scattered radiation, a member called anti-scattering grid (also referred to as simply "grid" hereinafter) is placed between the subject and the image sensor. This grid is an arrangement of radiation absorptive members, such as lead plates having thickness of less than approximately 1 mm, in grid or row formation, and reduces scattered radiation which arrives at the image sensor by absorbing scattered radiation advancing in random directions. However, even when this anti-scattering grid is utilized, a large amount of scattered radiation which is scattered from the subject reaches the image sensor, and causes deterioration of image contrast. For this reason, there is a need to further reduce the effect of scattered radiation. The present invention relates to a method of reducing scattered radiation.

Conventionally, a method of obtaining a radiation image is known in which the effect of scattered radiation is reduced by scattered radiation distribution obtained by utilizing the drop in contrast from the scattered radiation of the subject by an anti-scattering grid. More specifically, when an anti-scattering grid is used, its shade appears as stripes (also referred to as "grid image" hereinafter) in the image obtained by the image sensor. This grid-image appears as prominent shades when there is no scattered radiation, and becomes obscure when there is scattered radiation. Using the difference, it is possible to obtain a two-dimensional distribution of scattered radiation. A technique resembling this is disclosed in Japanese Patent Laid-Open No. S62-092662.

However, as in Japanese Patent Laid-Open No. S62-092662, it is not possible to accurately retrieve an amount corresponding to the scattered radiation merely by subtraction between pixels above which the grid exists. This is due to the fact that the pixel value of a pixel above which the grid exists is determined according to either equation (1) or equation (2) when there is no subject and when there is a subject, respectively.

Pixel value=irradiation component−grid component (1)

Pixel value=irradiation component−subject component+scattered component (2)

In the above equations, the pixel value on the left and each of the items on the right are values from logarithmic conversion of the X-ray amount that reaches the image sensor. The irradiation component is the pixel value that reaches the image sensor when there is no subject. The grid component is the pixel value of the grid shade, and the subject component is the pixel value of the subject shade. The scattered component is the pixel value corresponding to the amount of scattered radiation scattered from the subject. From the subtraction of equations (1) and (2), an amount [scattered component−subject component] can be obtained. However, this amount not only includes the scattered component, but also includes the subject component, and from this fact it is clear that it is not possible to obtain only the amount corresponding to the scattered radiation from the subtraction between pixels above which the grid exists. In other words, with the method disclosed in Japanese Patent Laid-Open No. S62-092662, it is not possible to gauge the amount of scattered radiation. In order to determine whether there is a large amount of scattered radiation, it is necessary to eliminate the effect related to the subject component.

SUMMARY OF THE INVENTION

The present invention provides a radiation image processing apparatus which is capable of determining whether there is a large amount of scattered radiation without being affected by a subject being imaged. Also, the present invention locally determines at each of the positions whether there is a large amount of radiation, and eliminates the effect of scattered radiation from the radiation image at each individual position thereby enhancing image contrast. Further, the present invention provides an X-ray radioscopy apparatus in which scattered radiation from the subject being imaged is small.

According to one aspect of the present invention, a radiation image processing apparatus which performs image processing on radiation images obtained by radiation imaging at a radiation imaging device having a grid on a front surface of a radiation detection unit for eliminating scattered radiation from a subject is provided. The radiation image processing apparatus includes a first extraction unit configured to extract a first grid image component arising from the grid in a first image data obtained from radiation imaging without passing through the subject, a second extraction unit configured to extract a second grid image component arising from the grid in a second image data obtained from radiation imaging through the subject, and a calculation unit configured to calculate a two dimensional distribution of abundance of scattered component by comparing the first grid image component and the second grid image component.

Further features of the present invention will become apparent from the following description of exemplary embodiments with reference to the attached drawings.

DESCRIPTION OF THE EMBODIMENTS

Various exemplary embodiments, features, and aspects of the present invention will be described in detail below with reference to the drawings.

The present invention focuses attention on the fact that scattered component can be separated into "scattered component of subject component" and "scattered component of grid component" and calculates abundance of scattered component by obtaining the scattered component for the grid component. Using FIGS. 3 and 4, scattered components of the grid component and of the subject component will be explained below.

Figure 3:
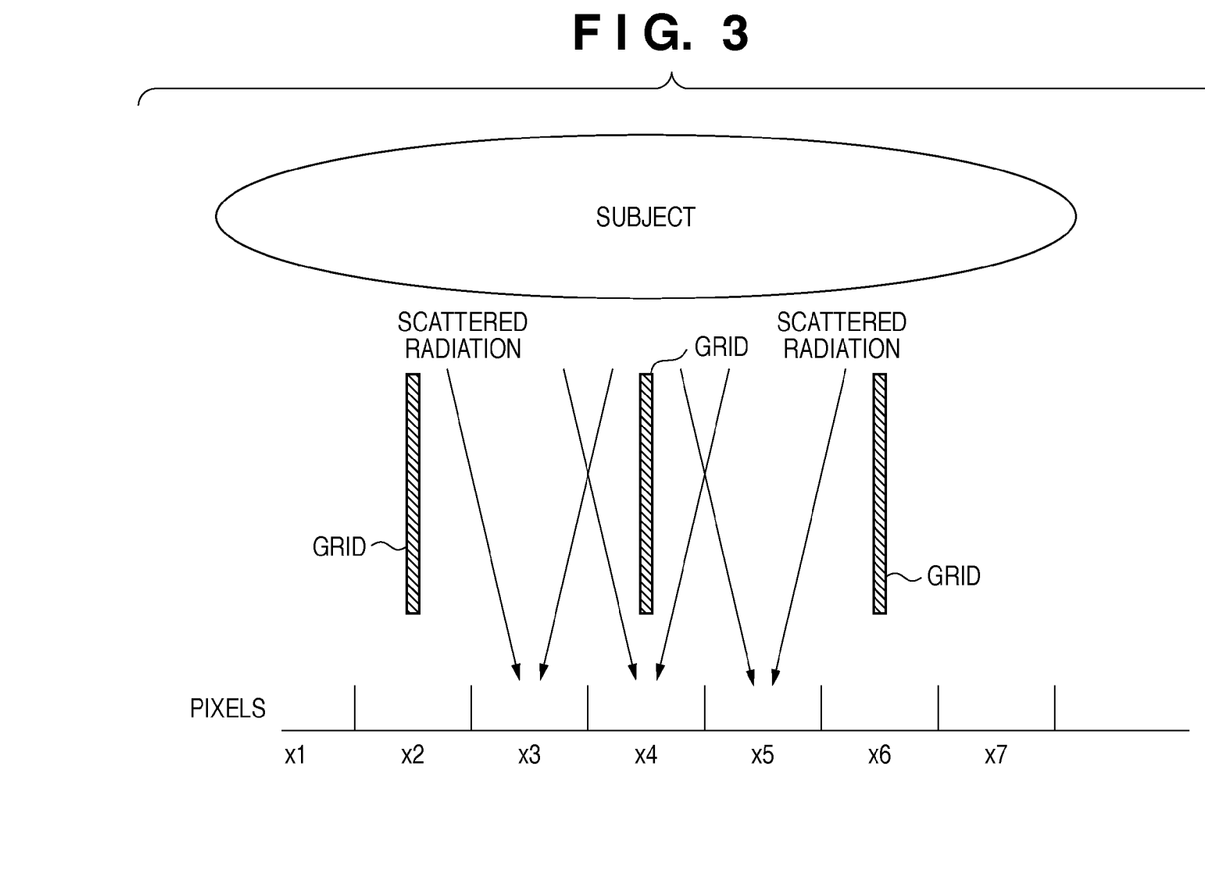
FIG. 3 is a schematic representation of the relationship between scattered radiation, grid and pixel, and illustrates a case in which angle of incidence of scattered radiation is close to being vertical.

FIG. 3 shows a case in which scattered radiation is irradiated on pixels at an angle which is close to being vertical. From the top to the bottom, a subject, grids, and pixels are placed in order. Scattered radiation generated at the subject reaches the pixels without being interrupted by the grids, and even pixel x4, above which a grid exists, encounters scattered radiation in the same fashion as pixels x3 and x5, above which no grid exists.

Figure 4:
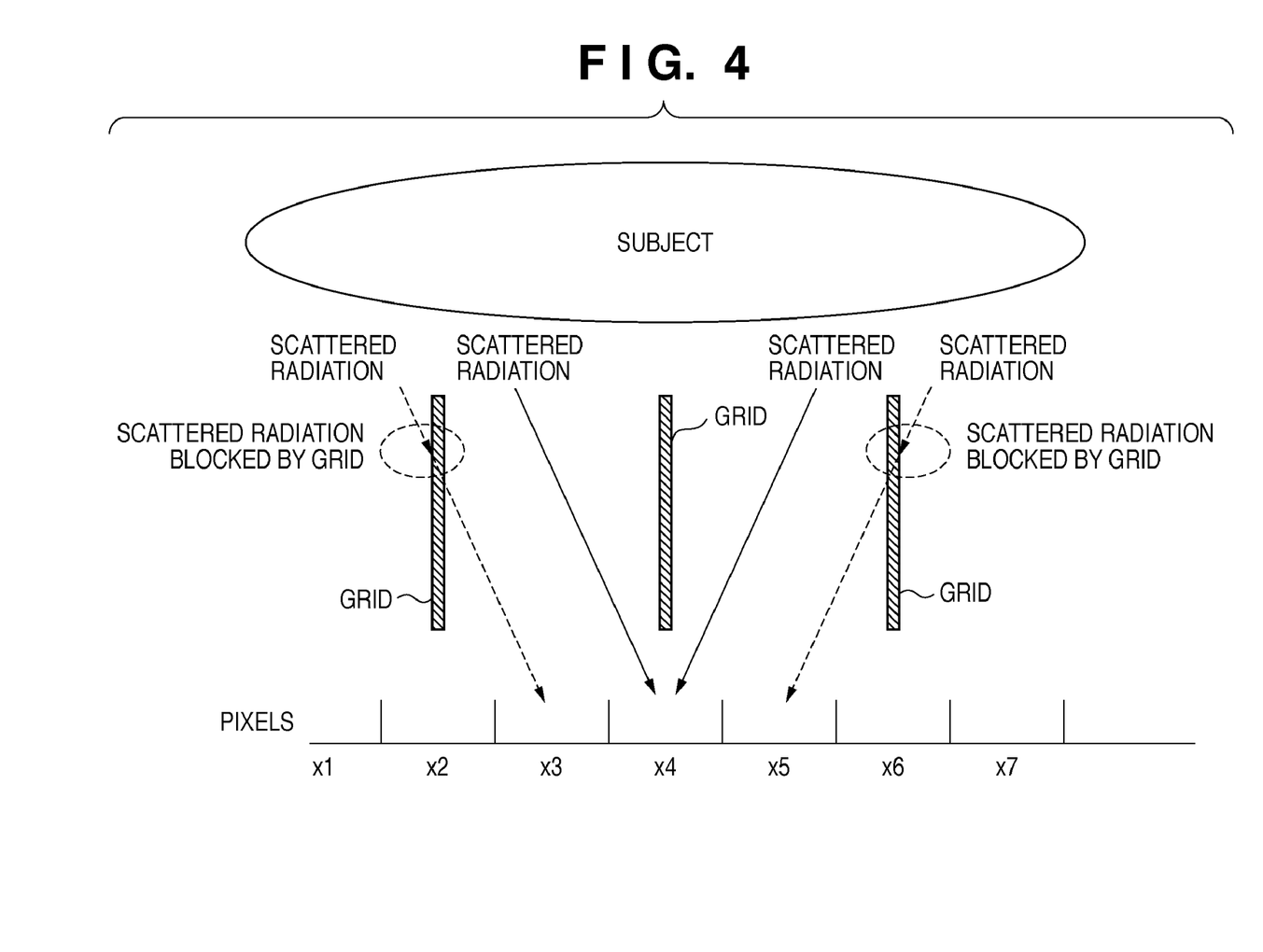
FIG. 4 is a schematic representation of the relationship between scattered radiation, grid and pixel, and illustrates a case in which angle of incidence of scattered radiation is shallow.

On the other hand, FIG. 4 illustrates a case in which scattered radiation reaches the pixels at a relatively large angle of incidence. Scattered radiation reaches pixel x4, above which a grid exists, but for pixels x3 and x5, above which no grid exists, scattered radiation is interrupted by the grids, preventing them from reaching the pixels. In other words, pixel value of pixels above which no grid exists is assigned according to the following formula:

Pixel value=irradiation component−subject component+scattered component 1   (3)

Also, pixel value of pixels above which grids exist is assigned according to the following formula:

Pixel value=irradiation component−subject component+scattered component 1−grid component+scattered component 2   (4)

In the above equations (3) and (4), the scattered component 1 is the scattered radiation in which angle of incidence is small (i.e., the angle of incidence is closer to being vertical) and the scattered component 2 is the scattered radiation in which angle of incidence is large. The scattered component 1 is the "scattered component for the subject component", and the scattered component 2 is the "scattered component for the grid component".

Figure 5A:
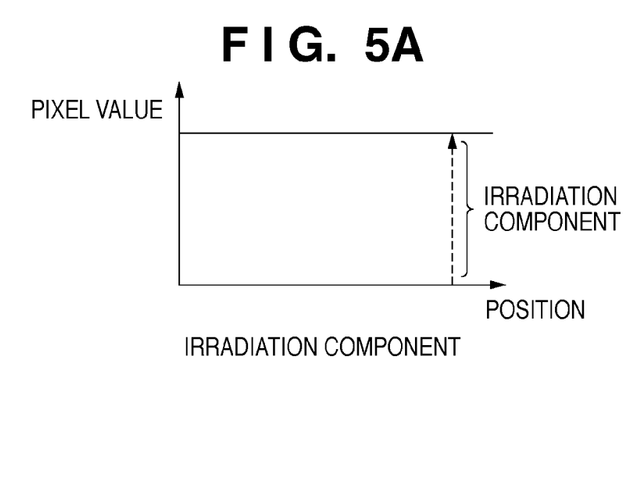
FIGS. 5A to 5C schematically show effect of scattered radiation on pixel value.
Figure 5B:
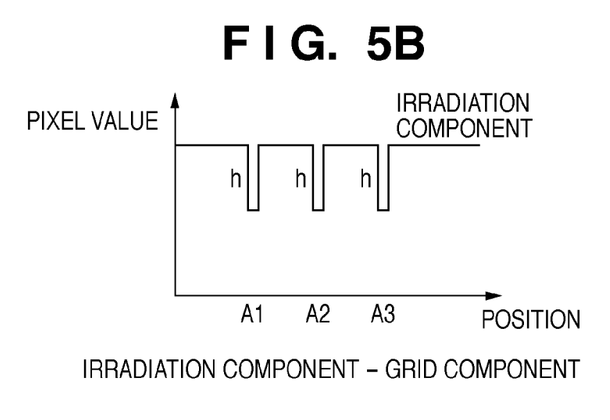
Figure 5C:
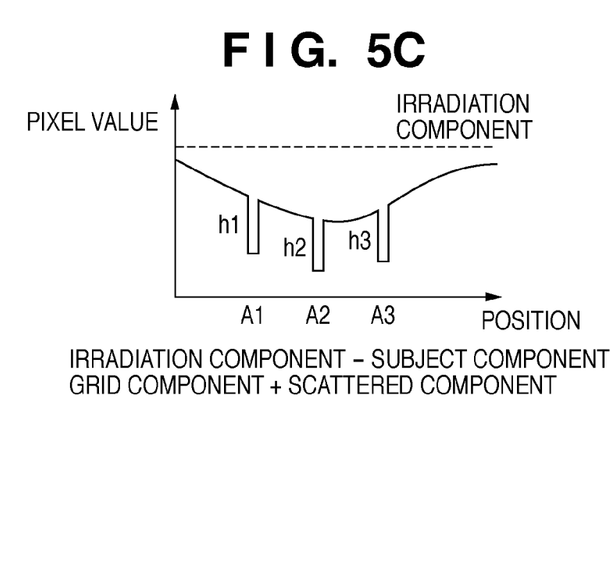

If pixel values of a single line from an image according to equations (3) and (4) are plotted, the obtained graph will look like FIG. 5C. FIG. 5A is a plot of pixel values when there is neither a subject nor a grid. Pixel values at every position correspond to luminance components at each of the respective positions. When a grid is mounted while keeping the luminance condition of FIG. 5A, pixel values change as shown in FIG. 5B. Positions A1, A2 and A3 are pixels on top of which the grid exists, and the pixel values of these positions decrease by a value h in comparison to those in the vicinity. FIG. 5C shows a plot of pixel values in a case where both a subject and a grid exists. Pixels on top of which a grid does not exist is expressed with equation (3), and those having a grid on top are expressed with equation (4). Positions A1, A2 and A3 are pixels on which a grid exists, and as shown in FIG. 5C, if the values of the pixels which correspond to the shadow of the grid are designated as h1, h2 and h3, then $h1 \leq h$, $h2 \leq h$, and $h3 \leq h$. Because scattered radiation exists, the pixel values corresponding to the grid shadow are smaller in comparison to the case shown in FIG. 5B. This decrease is the "scattered component for the grid component".

In the present invention, abundance of scattered radiation is obtained by comparing the difference between (1) pixel values of the grid shadow when there is no subject (first image data), and (2) pixel values of the grid shadow when there is a subject (second image data). More specifically, grid image components are extracted from each of the "first image data" and "second image data" and the two are compared in order to obtain abundance of scattered radiation.

The "scattered component of the grid component" is nearly proportionally related to the "scattered component of the subject component", and when the "scattered component of the grid component" is large, the "scattered component of the subject component" is also large. For this reason, it is possible to obtain abundance of scattered component by obtaining the "scattered component of the grid component" alone.

Further, the grid only exists at places above the pixels that are placed apart at intervals, and accordingly the abundance of scattered component is obtained from places that are placed apart at intervals. As such, abundance of scattered radiation at pixels on which no grid exists is obtained by interpolating with an interpolation function such as a zero-order interpolation or a first order interpolation. Following this procedure, it is possible to generate a two-dimensional distribution of abundance of scattered component using an interpolation function.

With a two-dimensional distribution of abundance of scattered component, it is possible to eliminate scattered component. This is because the absolute amount of the abundance of scattered component is almost proportional to the two-dimensional distribution of the calculated abundance of the scattered component. Accordingly, it is possible to eliminate scattered component only by subtracting a multiple of the "2-dimensional distribution of the abundance of scattered component" from the "second image data". As a result, it is possible to improve image contrast.

Another method of improving image contrast is to implement the sharpening process with higher intensity at places where scattered components are abundant using the two-dimensional distribution of the abundance of scattered component. As a simple method of adjusting how intense the sharpening process is to be, a method which adjusts gain of space frequency in a high frequency range by the Kernel coefficient of a 3×3 bypass filter can be used.

Further, an X-ray radioscopy apparatus according to an embodiment comprises a configuration in which the X-ray irradiation conditions are sequentially changed to reduce scattered radiation using the calculated abundance of scattered component. With this configuration, it is possible to observe radioscopic images under an X-ray irradiation condition with the least amount of scattered radiation. For this reason, in comparison to conventional devices, it is possible to improve image contrast.

In devices that are not capable of calculating abundance of scattered components, it is not possible to determine what should be changed in order to reduce scattered radiation. X-ray radioscopy apparatuses that are capable of calculating abundance of scattered components are helpful in this regard.

Embodiment 1

Figure 1:
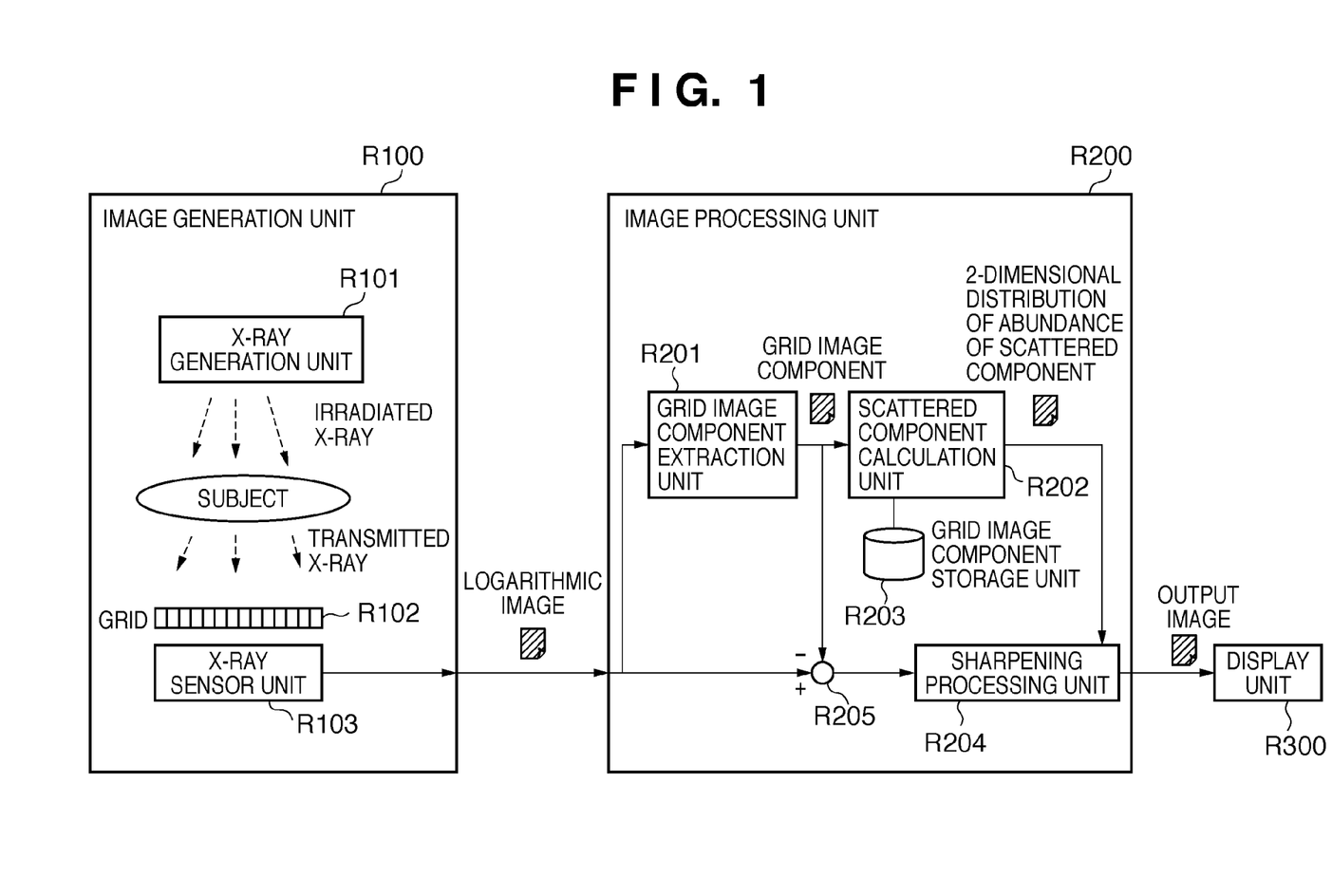
FIG. 1 is a block diagram showing the functional configuration of a radiation image processing apparatus according to embodiment 1.
Figure 6:
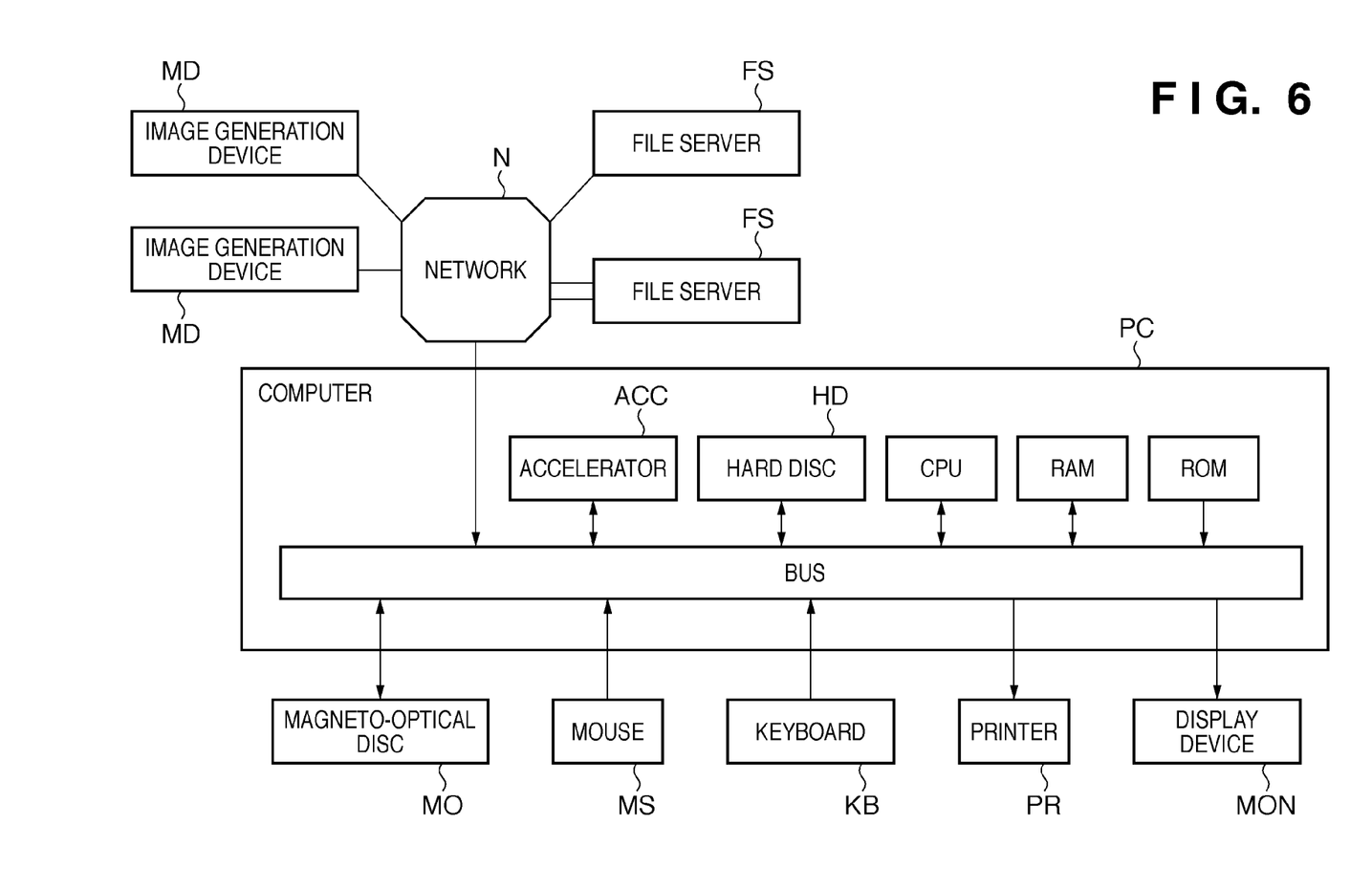
FIG. 6 is a block diagram showing the hardware configuration of the radiation image processing apparatus according to embodiments.
Figure 10A:
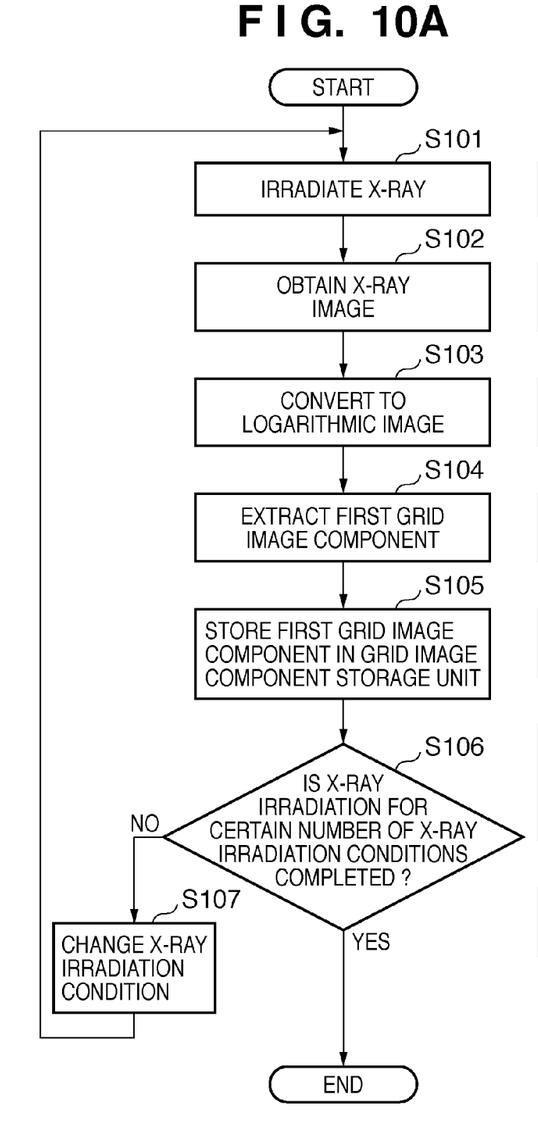
FIGS. 10A and 10B are flow charts indicating operation of the device according to embodiment 1 and embodiment 2.
Figure 10B:
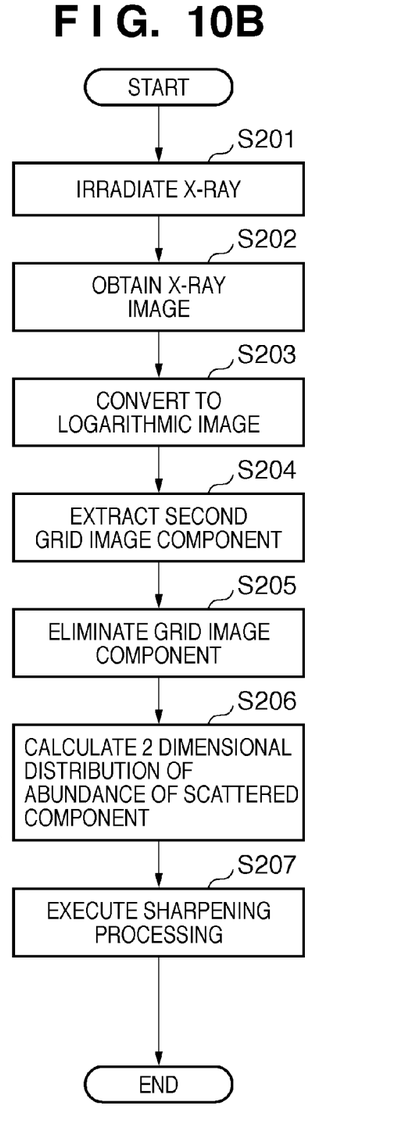

FIG. 1 is a block diagram showing functional configuration of a radiation image processing apparatus according to embodiment 1. FIGS. 10A and 10B are flow charts showing operation of the radiation image processing apparatus according to the present embodiment. FIG. 6 is a block diagram showing the hardware configuration of the radiation image processing apparatus according to the present embodiment. In the following, the function of each of the blocks in FIG. 1 will be explained in accordance with the order of the flowcharts shown in FIGS. 10A and 10B.

The program corresponding to each of the steps shown in FIGS. 10A and 10B is stored in a storage device such as a hard disc HD, a magneto-optical disc MO, a RAM or a ROM of a computer PC shown in FIG. 6. Actions described below are executed by the CPU reading out the program from the storage device, and executing the program in the order shown in the flow charts.

As an order of execution, the flow shown in FIG. 10A is executed first, and then the flow of FIG. 10B is subsequently executed. FIG. 10A is a flow chart of processing for storing grid image components when there is no subject. FIG. 10B is a flow chart of processing for improving image contrast by eliminating effect of scattered radiation when there is a subject.

First, in FIG. 10A, the trigger for "start" is generated by pressing of an X-ray irradiation button (not shown) by a user, which connected to an image generation unit R100 shown in FIG. 1.

As a radiation imaging device, the image generation unit R100 comprises an X-ray generation unit R101 which irradiates X-ray towards the subject, and an X-ray sensor unit R103 which functions as a radiation detection unit that detects the X-ray which has passed through the subject. Further, a grid R102 for eliminating scattered radiation from the subject is provided on the X-ray sensor unit R103.

At step S101, the X-ray generation unit 101 in FIG. 1 irradiates X-ray, which passes the grid R102 and arrives at the x-ray sensor unit R103. Although a subject is shown in FIG. 1, FIG. 10A illustrates a flow chart for cases in which no subject exists as discussed above, and the irradiated X-ray and the transmitted X-ray are the same in this case.

Subsequently, at step S102, the X-ray sensor unit R103 obtains an X-ray image by converting the X-ray that has arrived into electric signals.

Subsequently, at step S103, a logarithmic conversion unit (not shown) attached to the X-ray sensor unit R103 converts the X-ray image obtained at step S102 to a logarithmic image, and outputs this logarithmic image from the image generation unit R100. The output logarithmic image is input into an image processing unit R200.

At step S104, grid image components originating from the grid are extracted from the logarithmic image at a grid image component extraction unit R201 (first extraction). To be specific, grid image components are extracted by implementing a spatial filter which extracts spatial frequency of the grid. For the sake of simplicity, the grid image component when there is no subject will be referred to as a first grid image component.

Subsequently, at step S105, the first grid image component extracted from step S104 is stored at a grid image component storage unit R203 along with X-ray irradiation condition of the X-ray generation unit R101. The term X-ray irradiation condition used herein includes X-ray tube voltage and X-ray tube current (also referred to as "tube voltage" and "tube current", respectively).

At step S106, it is determined whether X-ray irradiation has ended or not for a certain number of X-ray irradiation conditions. If X-ray irradiation has not ended, the process advances to step S107. If X-ray irradiation has ended, that is the "end" of the process. At step S107, irradiation condition is changed to an X-ray irradiation condition that is yet to be used for irradiation among the certain number of X-ray irradiation conditions, and the process returns to step S101.

The certain number of X-ray irradiation conditions is related to step S206 to be discussed later, and are related to accuracy when calculating abundance of scattered radiation. Abundance of scattered radiation is calculated by comparing the first grid image component with a grid image component when there is a subject (also referred to as "second grid image component" hereinafter). However, it cannot be said that the X-ray irradiation conditions of the first grid image component and the second grid image components are always identical. For this reason, it is necessary to obtain and store the first grid image component under a plurality of X-ray irradiation conditions in advance, and then estimate the first grid image component under the X-ray irradiation conditions of the second grid image component when obtaining the second grid image component.

To be more specific, it is necessary to estimate the value of h from FIG. 5B. Because logarithmic images are used in the present embodiment, the value of h in FIG. 5B does not depend on the tube current, but rather depends only on the tube voltage. For this reason, for a system with a radiation image processing apparatus that is capable of changing the tube voltage within a range of 70 kV to 100 kV, X-ray is irradiated at voltages of, for example, 70 kV, 80 kV, 90 kV, 100 kV, and 110 kV, which are separated by increments of 10 kV. The Tube current can be kept constant at, for example, 4.0 mA. In such case, the certain number of x-ray irradiation conditions means the following 5 sets of conditions: (70 kV, 4.0 mA), (80 kV, 4.0 mA), (90 kV, 4.0 mA), (100 kV, 4.0 mA), (110 kV, 4.0 mA).

As discussed above, FIG. 10A is a flow chart of processing to store grid image components when there is no subject. Since this process needs to be performed only once, it can be performed at the time of installation of the radiation image processing apparatus, or can be performed on a regular basis in consideration of system deterioration due to age.

What comes next is FIG. 10B. The trigger for "start" is generated by the user's pressing of the X-ray irradiation button (not-shown) connected to the image generation unit R100 of FIG. 1. At step S201, the X-ray generation unit R101 of FIG. 1 irradiates X-ray, which passes through the grid R102, and arrives at the X-ray sensor unit R103.

Subsequently, at step S202, the X-ray sensor unit R103 obtains an X-ray image by converting the X-ray that has arrived at the sensor into electric signals.

Then, at step S203, a logarithmic conversion unit (not shown), which belongs to the X-ray sensor unit R103, converts the X-ray image obtained at step S202 to a logarithmic image and outputs the logarithmic image to the image generation unit R100. The output logarithmic image is input to the image processing unit R200.

At step S204, a grid image component is extracted from the logarithmic image at the grid image component extraction unit R201 (second extraction). To be more specific, grid image component is extracted by implementing on the logarithmic image a spatial filter which extracts spatial frequency(s) of the grid. This grid image component is referred to as the second grid image component, as was already discussed at step S106 of FIG. 10A.

Subsequently at step S205, the second grid image component extracted at step S204 is subtracted from the logarithmic image input to the image processing unit R200. This subtraction is performed at a subtraction unit R205. This processing is not directly related to the goal of the present invention which is to "eliminate the effect of scattered radiation", but is nevertheless an important process for improving the quality of radiation images. It was discussed above that the shadow of the anti-scattering grid appears as stripes on the image obtained by the image sensor. This stripe-patterned image information is visually very bothersome when making observations, and elimination of the grid image component is desired.

Subsequently, at step S206, a two-dimensional distribution of abundance of scattered component is calculated at a scattered component calculation unit R202. First, the first image under the X-ray irradiation condition at step S201 is estimated. To be more specific, the value of h in FIG. 5B is estimated. In order to do this, interpolation processing is performed using a plurality of first images stored ahead of time in the grid image component storage unit R203. For example, a hypothetical case is considered in which first images having conditions of (70 kV, 4.0 mA) and (80 kV, 4.0 mA) are stored, and the X-ray irradiation condition at step S201 is (75 kV, 3.0 mA). In such a case, the value of h for the condition (75 kV, 3.0 mA) is predicted by linear interpolation which can be represented as, for example, a formula shown below.

$$\{h(70\ kV, 4.0\ mA) + h(80\ kV, 4.0\ mA)\}/2$$

The method of measuring the grid component H is not limited to this, and can also use an interpolation function of a higher order.

Next, abundance of scattered radiation in an image having a grid above the pixels is calculated by comparing the difference between the predicted grid component h and the grid components of the second grid image component (which are h1, h2 and h3 in FIG. 5C). The term abundance of scattered radiation as used here means scattered component 2 in equation (4).

Next, abundance of scattered radiation is predicted for pixels above which no grid exists. To be more specific, using the abundance of scattered radiation for pixels having a grid above, interpolation processing is performed by applying a linear interpolation or an interpolation function of a high order. With this interpolation processing, "a two-dimensional distribution of abundance of scattered radiation" is calculated, and is output from the scattered component calculation unit R202.

At step S207, sharpening process is performed at the sharpening processing unit R204 in a manner in which the larger the value of the "two dimensional distribution of abundance of scattered radiation" output at step S206, the higher the level of emphasis of the sharpening process. For example, for locations having a large value of "two dimensional distribution of scattered radiation", a higher range of the spatial frequency is amplified. Here, the image to be applied with sharpening process is the image which is output by the subtraction unit R205. As a specific example of a sharpening process, following coefficients can be considered when performing convolution of a 3×3 spatial filter such as the one shown in FIG. 12 at every position.

Figure 12:
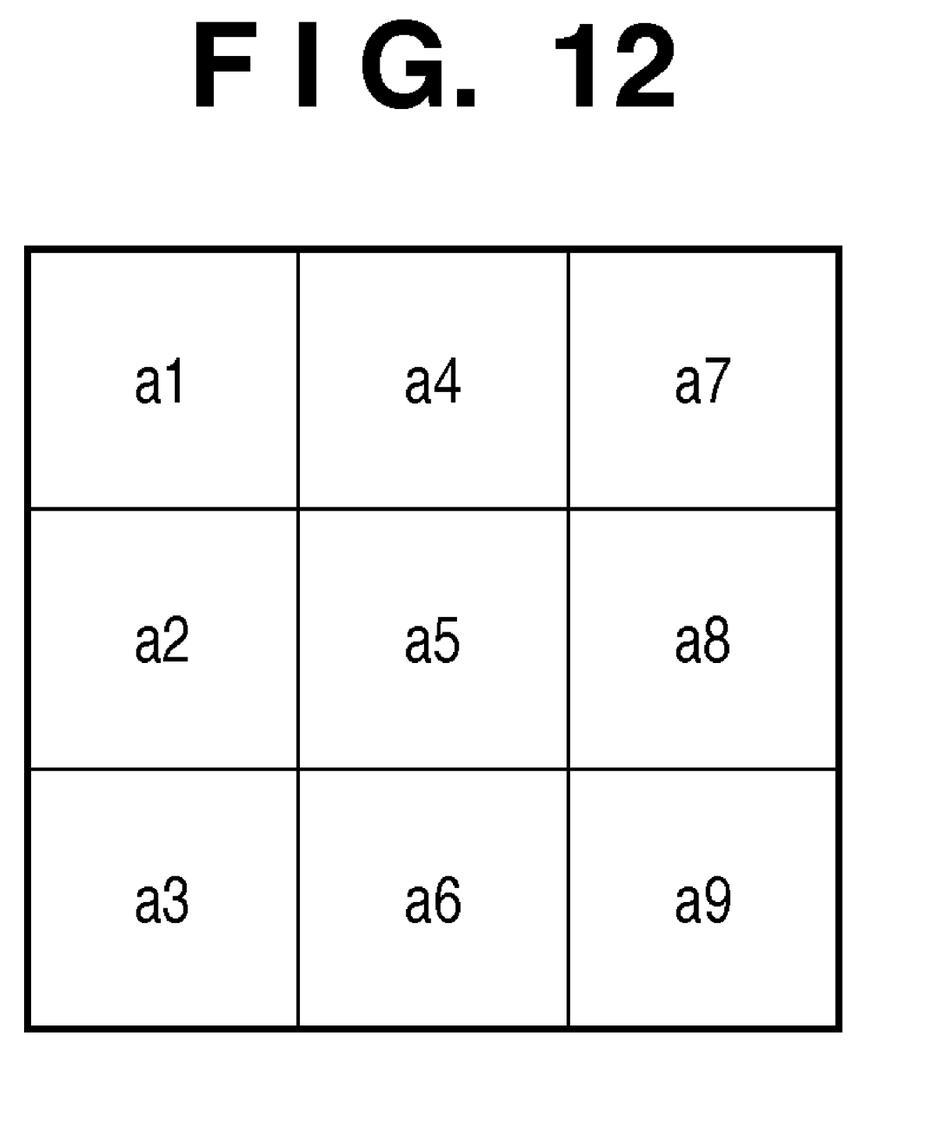
FIG. 12 is a diagram which explains an example of a sharpening method by a sharpening processing unit.

$a1 = A(-1/9)$
$a2 = A(-1/9)$
$a3 = A(-1/9)$
$a4 = A(-1/9)$
$a5 = A(1-1/9)+1$
$a6 = A(-1/9)$
$a7 = A(-1/9)$
$a8 = A(-1/9)$
$a9 = A(-1/9)$

In these filter coefficients, A is a parameter for adjusting intensity of sharpening process, wherein higher values indicate heavier emphases. If the "two-dimensional distribution of abundance of scattered radiation" is set as B, it is possible to achieve "amplifying higher range of spatial frequency for locations having a large value of 'two dimensional distribution of scattered radiation'" using a relationship such as $A = kB$ (k is a proportional constant).

A sharpening processing unit R204 executes sharpening process as discussed, and outputs an output image. The output image is input into a display unit R300, which is then displayed on the display, and the process shown in the flow chart 10 (b) arrives at "end".

On the other hand, a technique of removing a grid image has been suggested previously (for example, Japanese Patent Laid-Open No. 2006-272013 and Japanese Patent Laid-Open No. 2003-150954). The first and second grid image components can be extracted and compared using these prior art techniques.

In the present embodiment, step S206 was performed after step S205, but either one can be performed before the other. Also, the two steps can be performed simultaneously in parallel processing.

Further, although images were converted to logarithmic images at steps S103 and S203 in the present embodiment, each of the processing can be performed without converting images to logarithmic images. In such cases, additions that followed logarithmic conversion are performed as multiplications, and subtractions that followed logarithmic conversion are performed as divisions.

Further, a noise reduction processing unit for reducing noise of radiation images can be added in front of the sharpening processing unit R204 shown in FIG. 1 or at the back of it. With this addition of the noise reduction processing unit, the quality of the output images, which are outputs of the image processing unit R200, improves.

Lastly, the overall configuration of the system will be discussed.

In FIG. 6, the computer PC is connected to one or a plurality of image generating devices MD via a network N. Alternatively, the present invention can equally be implemented by having images captured by an image capturing device (not shown) stored in the file server FS ahead of time, and handling the file server in the same manner as an image generation device.

The image generation unit R100 in the functional block diagram of FIG. 1 corresponds to an image generation device MD. In FIG. 6, the image generation device MD is connected to the computer PC via the network N, but the connection can also be made without going through the network. For example, it is also possible to directly connect the computer PC and the image generation device MD one to one.

The image processing unit R200 and the display unit R300 of FIG. 1 can be realized by the computer PC and its peripheral apparatuses installed within. As an example, the image processing unit R200 and the display unit R300 can respectively be realized by a program stored in a hard disc HD and a monitor MON shown in FIG. 6. In such case, the program stored in the hard disc HD is read out to the RAM by an input of a user (not shown), and, as discussed, the CPU performs the program in sequence to realize the functions discussed above, and the result of image processing is displayed on the display device MON. In this example, devices such as a CRT monitor, a liquid crystal display, etc, can be utilized as the display device MON.

Further, the program executed in the present embodiment needs not be stored in a hard disc HD. For example, the program can be stored on a magneto-optical disc MO which is connected to the computer PC as an external peripheral, or on a file server which is connected via the network. Alternatively, the image processing unit R200 and the display unit R300 of the present embodiment can be realized as an exclusive hardware accelerator ACC mounted on the computer PC partially or entirely.

Embodiment 2

The configuration of the first embodiment discussed above is mainly for the purpose of improving contrast of radiation images. On the other hand, the configuration of a second embodiment to be explained below not only focuses on improvement in contrast of radiation images, but also aims to reduce operator's exposure to radiation.

An operator who is performing a surgery is exposed to radiation due to generation of scattered radiation from the subject, even if the operator is not directly irradiated. Since radiation exposure to scattered radiation is not direct, the amount of radiation the operator receives is smaller than the amount that the subject receives. However, even if the amount of radiation per operation may be small, daily exposure to radiation from the total operation time could add up to a very large.

The foremost priority during an operation is clarity with which the subject is seen, and image quality is dependent on tube voltage and tube current which together make up a set of X-ray irradiation condition. Although it is not possible to change type and shape of the subject, it is possible to change the X-ray irradiation condition. For this reason, X-ray radioscopy apparatuses and X-ray radioscopic imaging apparatuses change X-ray irradiation conditions for every image in order to improve image quality, and selects X-ray irradiation conditions that satisfy the aimed image quality. Image quality is related to the amount of irradiated X-ray, and image quality will be nearly unchanged if the subject and the amount of irradiated X-ray remain the same. Also, when the X-ray irradiation condition has been determined, the amount of irradiated X-ray is uniquely determined accordingly.

In the present embodiment, if the amount of irradiated X-ray obtained under the X-ray irradiation condition selected by the X-ray radioscopy apparatus is represented by $\alpha$, an X-ray irradiation condition which generates $\alpha$ is selected from a plurality of X-ray irradiation conditions. Then, an X-ray image is obtained by irradiating X-ray using the selected X-ray irradiation condition, and the X-ray irradiation condition which reduces the scattered radiation to a minimum is searched for.

Figure 2:
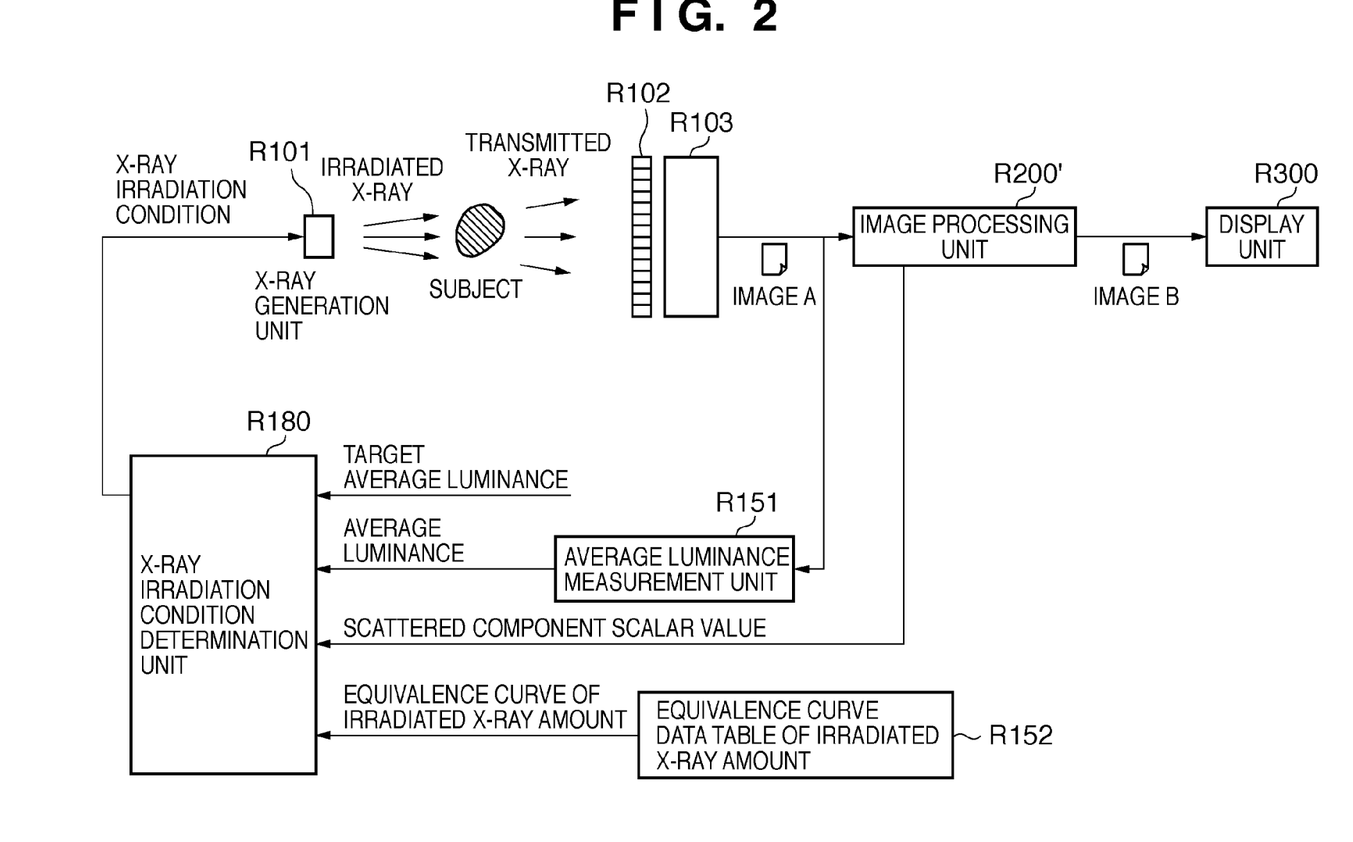
FIG. 2 is a block diagram showing the functional configuration of an X-ray radioscopy apparatus according to embodiment 2.
Figure 7:
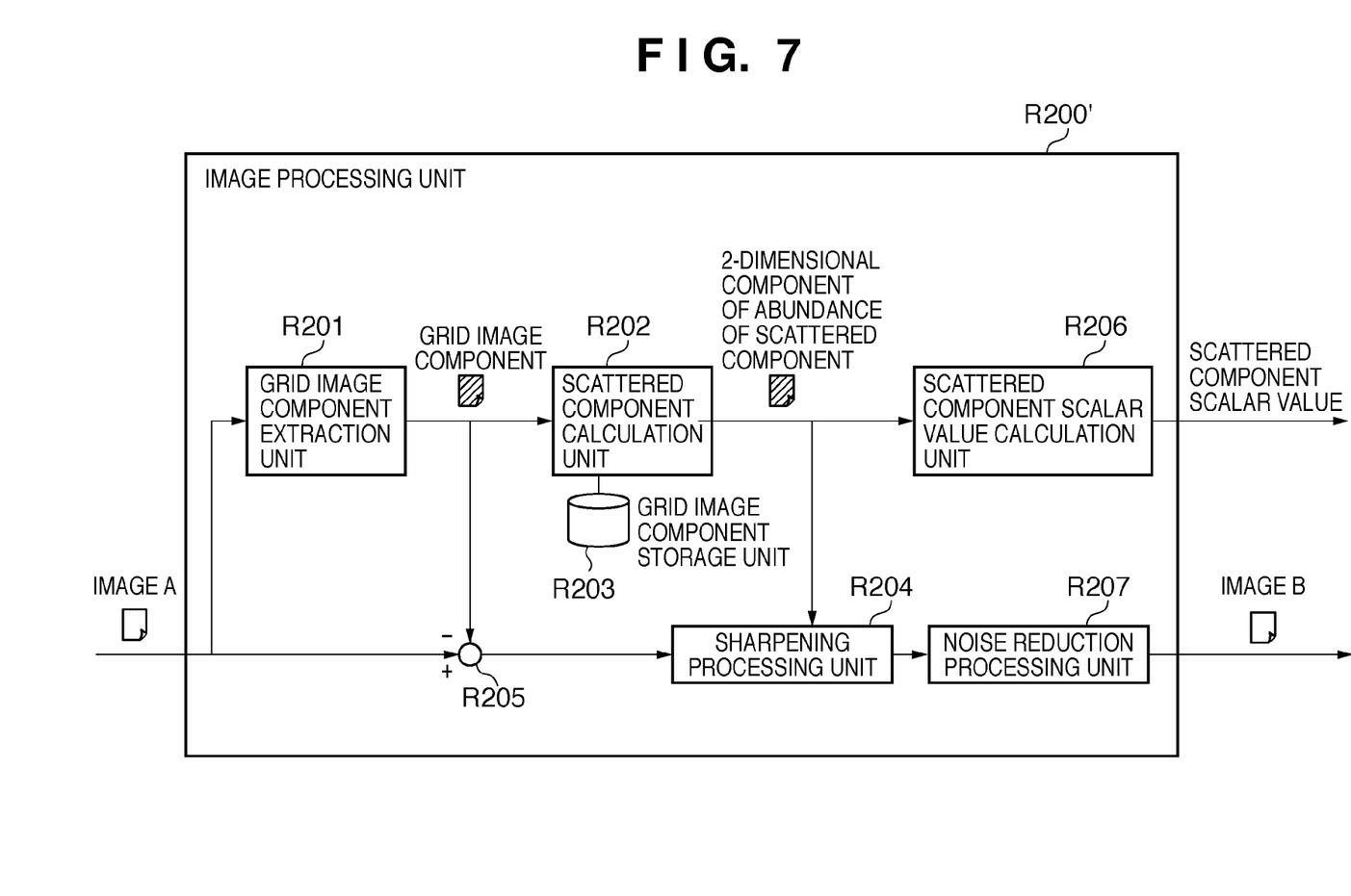
FIG. 7 is a block diagram showing the functional configuration of an image processing unit according to embodiment 2.
Figure 11:
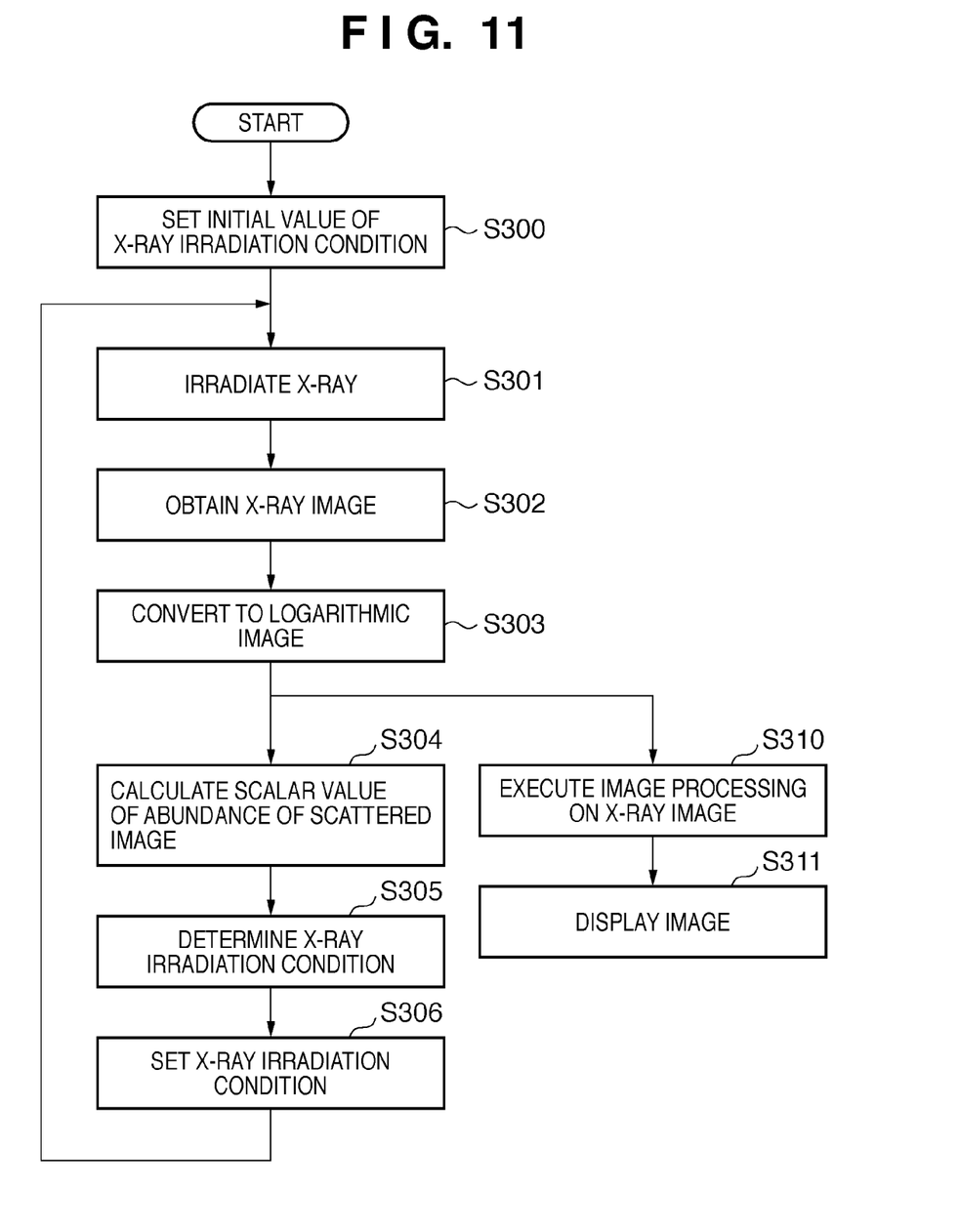
FIG. 11 is a flow chart indicating the operation of the device according to embodiment 2.

FIG. 2 is a block diagram showing functional configuration of an X-ray radioscopy apparatus according to the present embodiment, and FIG. 7 is a block diagram showing the functional configuration of the image processing unit of the present embodiment in detail. FIGS. 10A and 11 are flow charts showing control processing of the X-ray radioscopy of the present embodiment. The X-ray radioscopy apparatus is also one of radiation image processing apparatuses, and its basic configuration is identical to that of the first embodiment. Since the explanation for FIG. 10A is identical to the first embodiment, only the differences will be explained below in accordance with the order of the flow chart of FIG. 11.

As the order of execution, the flow shown in FIG. 10A is executed first, and then the flow of FIG. 11 is executed. FIG. 10A is a flow chart for the processing to store grid image component when there is not subject, and FIG. 11 is a flow chart for the processing to search for an X-ray irradiation condition which improves image contrast by eliminating effect of scattered radiation when there is a subject.

In FIG. 11, the trigger for "start" is generated by receiving an order to irradiate X-ray. For many X-ray radioscopy apparatuses, an order to irradiate X-ray is made by pressing a foot pedal or an irradiation button.

Following "start", step S300 is executed. At step S300, at the X-ray irradiation condition determination unit R108 of FIG. 2, a pre-stored initial value of X-ray irradiation condition is read out, and sets the X-ray irradiation condition. A value which is well suited for the part being observed is set as this initial value of X-ray irradiation condition. For example, when a thick part is to be observed, an X-ray irradiation condition in which the intensity of X-ray is large is used, and when a thin part is to be observed, an X-ray irradiation condition in which the intensity of X-ray is small is used. The present invention is not limited to any specific initial value of X-ray irradiation condition, and can also use arbitrary values.

Subsequently, step S301 is executed. At step S301, X-ray is generated at the X-ray generation unit R101 according to the X-ray irradiation condition set at step S300. The irradiated X-ray generated from the X-ray generation unit R101 penetrates through the subject, passes the grid F102 and arrives at the X-ray sensor unit R103.

Subsequently, step S302 is executed. At step S302, an X-ray image is obtained at the X-ray sensor unit R103.

Step S303 is executed next. At step S303, the X-ray image obtained at step S302 is converted to a logarithmic image. This logarithmic image is referred to as image A in FIG. 2. This image A is input to an average luminance measurement unit R151 and the image processing unit R200.

Subsequently, steps S304 and S310 are executed. These two steps are not conditional branching but rather simultaneously executed, and operate in parallel. At step S304, a grid image component is extracted at the grid image component extraction unit R201, and calculates a "two dimensional distribution of abundance of scattered component" at the scattered component calculation unit R202.

The process up until this point is identical to that of the first embodiment. However, in the present embodiment, the "two dimensional distribution of abundance of scattered image" is integrated and output as "scattered component scalar value" at a scattered component scalar value calculation unit R206.

At Step S310, as in the first embodiment, the grid image component is eliminated at the subtraction unit R205 and the sharpening process is performed according to the size of the value of the "two dimensional distribution of abundance of scattered distribution" at the sharpening processing unit R204. Then, noise which is particular to radiation images is processed for reduction at a noise reduction processing unit R207, and outputs image B. The output image B is displayed on the display unit R300 of FIG. 2 at step S311.

Figure 8A:
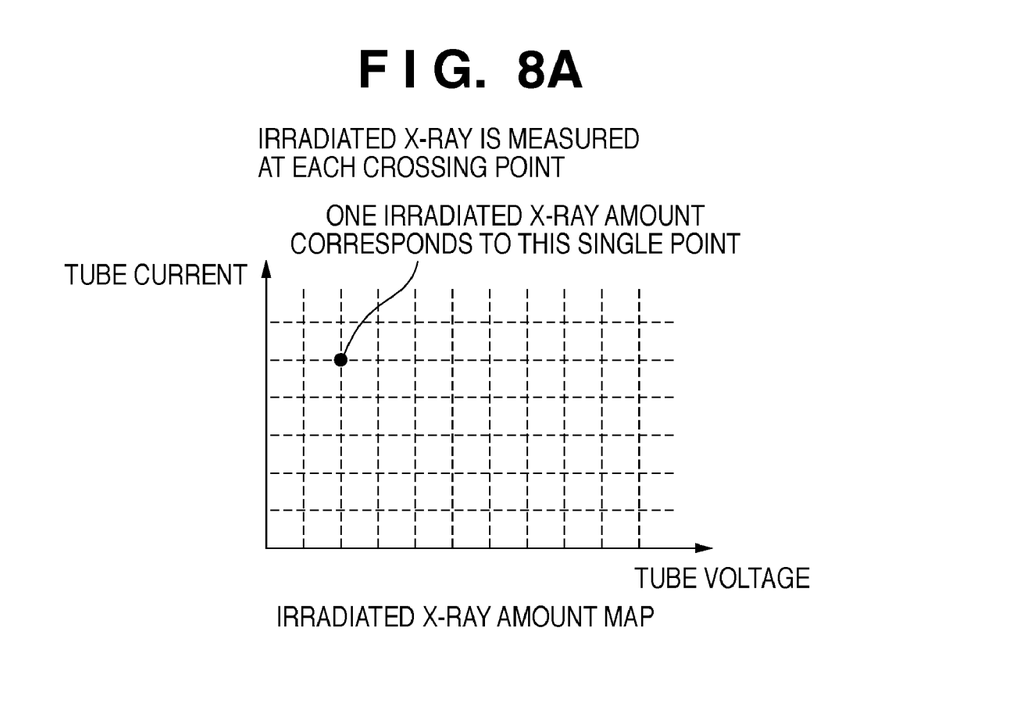
FIGS. 8A and 8B explain an equivalence curve data table of irradiated X-ray amount.
Figure 8B:
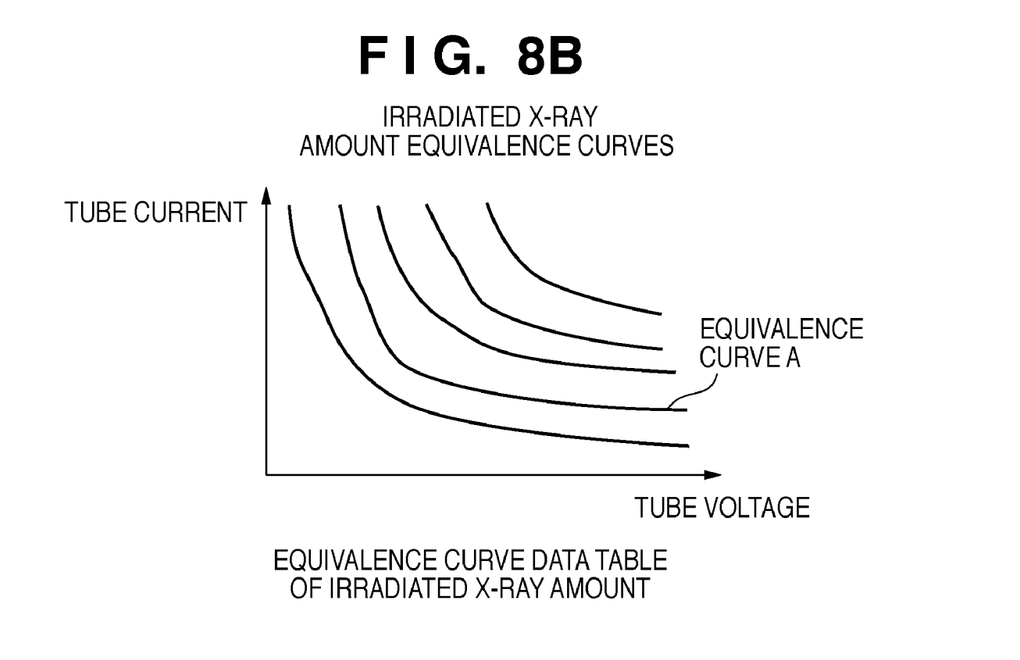

Step S305 is executed subsequently. At step S305, an X-ray irradiation condition for the next round of X-ray generation is determined at the X-ray irradiation condition determination unit R180. From the beginning until a few rounds, search is made for an X-ray condition which makes the average luminance value of the screen output by the average luminance measurement unit R151 equal to a targeted average luminance value. After the average luminance value becomes equal to the targeted average luminance value, an X-ray irradiation condition which reduces scattered radiation to a minimum is searched for using an irradiated X-ray amount equivalence curve data table R152 and the scattered component scalar value while keeping the targeted average luminance value. The term "round" indicates a loop that progresses from step S301 to step S306 which then returns back to step S301. Further, the irradiated X-ray amount equivalence curve data table R152 is data such as those shown in FIG. 8B and FIG. 9A. The irradiated X-ray amount is the amount of X-ray irradiated by the X-ray generation unit, and is an amount which is uniquely defined for each set of X-ray tube voltage and X-ray tube current. First, the irradiated X-ray amount is measured while changing the X-ray tube voltage and X-ray tube current in small increments as shown in FIG. 8A. Subsequently, points having identical values of irradiated X-ray amount are connected with a line. From this, data such as that shown in FIG. 8B is obtained.

As discussed above, irradiated X-ray amount is related to image quality, and if the subject and the irradiated X-ray amount remain the same, image quality will also remain nearly the same. For this reason, when an image is captured using a combination of X-ray tube voltage and X-ray tube current that satisfy the equivalence curve A of FIG. 8B, nearly identical image qualities will be obtained from any random combinations.

As one of the methods of changing X-ray irradiation condition to make the average luminance value equal to the targeted average luminance value, the following method is available. When the average luminance value is smaller than the targeted average luminance value, change is made to increase the irradiated X-ray amount from the current value. On the other hand, when the average luminance value is equal to or larger than the targeted average luminance value, the irradiated X-ray amount is decreased from the current value. These methods of changing the X-ray irradiation conditions are well known methods in the field pertaining to X-ray radioscopy apparatuses, and many of such methods are suggested (for example, Japanese Patent Laid-Open No. H07-183094).

In the present embodiment, the operation which is unique in comparison to examples of conventional techniques is the operation which is performed after the average luminance value is made equal to the targeted average luminance value. First, an equivalence curve which passes through the X-ray irradiation condition that achieves the targeted average luminance value is calculated, then X-ray is irradiated according to an X-ray irradiation condition which exists on the equivalence curve, and scattered component scalar values at each of the X-ray irradiation conditions are stored.

Figure 9A:
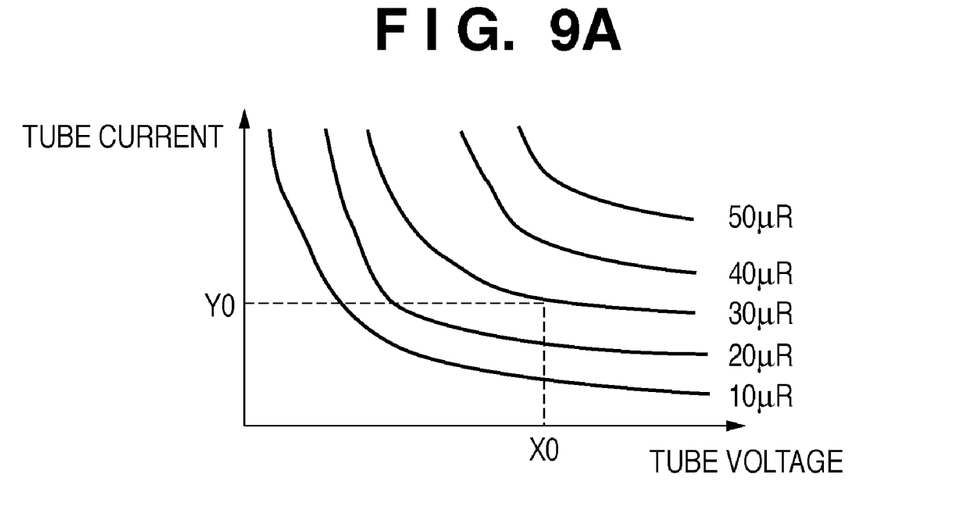
FIGS. 9A and 9B explain a method of using the equivalence curve data table of irradiated X-ray amount.
Figure 9B:
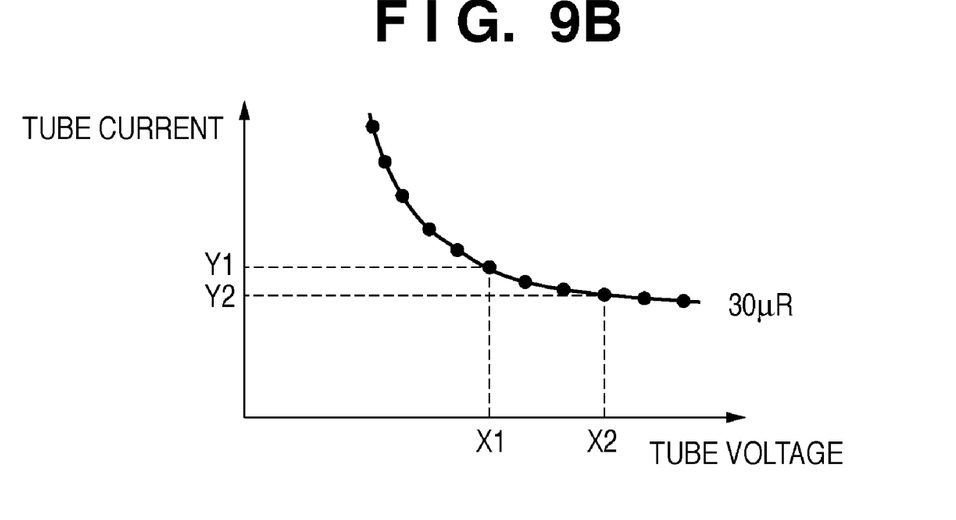

For example, when the X-ray irradiation condition which achieves the targeted average luminance value is X0 for the X-ray tube voltage and Y0 for the X-ray tube current in FIG. 9A, it can be understood that the irradiated X-ray amount is 30 µR. In other words, it can be understood that the equivalence curve which passes through an X-ray irradiation condition that achieves the target average luminance value is the curve of 30 µR. Subsequently, as shown in FIG. 9B, X-ray is irradiated using a plurality of x-ray irradiation conditions that exist on the curve of 30 µR. A plurality of X-ray irradiation conditions are two sets of conditions, one of which is (X-ray tube voltage=X1, X-ray tube current=Y1), and the other is (X-ray tube voltage=X2, X-ray tube current=Y2). Without restricting to these two, every black point shown on the curve of 30 µR in FIG. 9B can be considered as the plurality of X-ray irradiation conditions.

After irradiating according to the plurality of X-ray irradiation conditions, the X-ray irradiation condition having the smallest scattered component scalar value is searched for, and from thereafter X-ray is irradiated using this X-ray irradiation condition. However, in situations in which the subject being irradiated goes through change, such as the subject having moved, the operation returns to the initial operation. This is because the average luminance value is no longer equal to the targeted average luminance value once the subject has moved.

As discussed, in the present embodiment, a combination with the smallest scattered radiation is selected from numerous combinations of X-ray tube voltage and current which satisfy the equivalence curve. In other words, it is possible to select an X-ray irradiation condition with the least amount of scattered radiation while keeping the image quality essentially the same. For this reason, in comparison to conventional techniques, the operator's exposure to radiation is reduced, and at the same time radioscopic images with improved contrast can be obtained.

In this embodiment, the term "image quality" mentioned above is the average luminance of pixel value of X-ray images. Image quality is not limited to average luminance, and can also be other index values. Such index values need to have a positive or negative relationship with the irradiated X-ray amount. This is because, if image quality is independent of irradiated X-ray amount, image quality will change when X-ray is irradiated according to X-ray irradiation conditions that are present on the irradiated X-ray amount equivalence curve at step S305. The present embodiment is characterized in that it obtains the X-ray irradiation condition with the smallest scattered radiation without changing image quality, and for this a positive or negative relationship is required.

In the present embodiment, a positive relationship is found. This is because when the average luminance increases the transmitted X-ray amount also increases. Also, if the subject remains the same, when the transmitted X-ray amount increases the irradiated X-ray amount also increases. Thus the average luminance and irradiated X-ray amount have a positive relationship.

Further, when the average luminance increases the transmitted X-ray amount also increases. If the transmitted X-ray amount increases, SN ratio also increases. Generally, images with a large SN ratio is said to have good image quality. Thus image quality can be substituted with average luminance.

With the configuration of the present embodiment, it is possible to reduce radiation exposure to the operator and at the same time provide a radioscopic image with improved image contrast when compared to conventional X-ray radioscopy apparatuses.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-278610, filed Oct. 29, 2008, which is hereby incorporated by reference herein in its entirety.

What is claimed is:

1. An X-ray radioscopy apparatus having a grid on a front surface of a radiation detection unit for eliminating radiation from a subject, said apparatus comprising:
    a first extraction unit configured to extract a first grid image component arising from said grid in a first image data obtained from radiation imaging without passing through the subject;
    a second extraction unit configured to extract a second grid image component arising from said grid in a second image data obtained from radiation imaging through the subject;
    a calculation unit configured to calculate abundance of scattered component as a scalar value by comparing said first grid image component and said second grid image component; and
    a determination unit configured to determine an X-ray irradiation condition to reduce said scalar value calculated by said calculation unit.

2. The X-ray radioscopy apparatus according to claim 1, further comprising a storage unit configured to store an equivalence curve data table of irradiated X-ray amount related to X-ray irradiation condition,
    wherein said calculation unit obtains X-ray images by radiation imaging under a plurality of X-ray irradiation conditions that exist on the equivalence curve from said equivalence curve data table, and calculates said scalar values for each, and
    wherein said determination unit selects the X-ray irradiation condition which has the smallest scalar value among scalar values calculated by said calculation unit.

3. A method of controlling an X-ray radioscopy apparatus having a grid on a front surface of a radiation detection unit for eliminating radiation from a subject, comprising steps of:
    extracting a first grid image component arising from the grid in a first image data obtained from radiation imaging without passing through the subject;
    extracting a second grid image component arising from the grid in a second image data obtained from radiation imaging through the subject;
    calculating abundance of scattered component as a scalar value by comparing the first grid image component and the second grid image component; and
    determining an X-ray irradiation condition to reduce the scalar value calculated in said calculation step.

4. A non-transitory computer-readable medium storing, in executable form, a computer program for controlling an X-ray radioscopy apparatus having a grid on a front surface of a radiation detection unit for eliminating radiation from a subject, the program comprising code for performing the following steps:
    extracting a first grid image component arising from the grid in a first image data obtained from radiation imaging without passing through the subject;
    extracting a second grid image component arising from the grid in a second image data obtained from radiation imaging through the subject;
    calculating abundance of scattered component as a scalar value by comparing the first grid image component and the second grid image component; and
    determining an X-ray irradiation condition to reduce the scalar value calculated in said calculation step.

* * * * *